United States Patent [19]

Amano et al.

[11] Patent Number: 5,077,011
[45] Date of Patent: Dec. 31, 1991

[54] DRY ANALYTICAL ELEMENT CONTAINING SELF-DEVELOPING SUBSTRATE FOR USE IN ANALYSIS OF LIQUID

[75] Inventors: Yoshikazo Amano; Harumi Katsuyama, both of Asaka, Japan

[73] Assignee: Fuji Photo Film Co., Ltd., Kanagawa, Japan

[21] Appl. No.: 939,856

[22] Filed: Dec. 9, 1986

[30] Foreign Application Priority Data

Dec. 10, 1985 [JP] Japan ................. 60-277414

[51] Int. Cl.$^5$ ............. C12Q 1/00; G01N 21/77; G01N 31/22; 435 4; 435 21; 422 55; 422 56; 422 57; 422 58; 422 59; 422 60; 422 61; 436 170
[52] U.S. Cl. ..................... 422/56; 422/57; 422/58; 435/4; 435/21; 436/170
[58] Field of Search ............... 435/4, 21; 422/55, 56, 422/57, 58, 59, 60, 61; 436/170

[56] References Cited

U.S. PATENT DOCUMENTS

| 4,069,017 | 1/1978 | Wu et al. | 422/56 X |
| 4,153,668 | 5/1979 | Hiu et al. | 422/56 |
| 4,274,832 | 6/1981 | Wu et al. | 422/56 X |
| 4,557,901 | 12/1985 | Koyama et al. | 422/56 |
| 4,576,793 | 3/1986 | Koyama et al. | 422/56 |
| 4,671,937 | 6/1987 | Katsuyama et al. | 422/56 |

FOREIGN PATENT DOCUMENTS

| 1519465 | 7/1978 | United Kingdom . |
| 2002514 | 2/1979 | United Kingdom ............. 422/57 |
| 1571265 | 7/1980 | United Kingdom . |

*Primary Examiner*—John S. Maples
*Attorney, Agent, or Firm*—McAulay Fisher Nissen Goldberg & Kiel

[57] ABSTRACT

A dry analytical element for use in the measurement of activity of enzyme in an aqueous liquid, such as, body fluid, having one or more water-retaining layers. The enzyme has an optimum pH in a in pH range within which the dissociation of p-nitrophenol is insufficient for color formation. The layers of the element comprise a self-developing substrate having p-nitrophenol group attached to the molecular structure through an ether or ester linkage and a cationic polymer, said self-developing substrate and said cationic polymer being incorporated separately in different water-retaining carriers which are arranged to allow the layers to have liquid contact with each other.

11 Claims, No Drawings

DRY ANALYTICAL ELEMENT CONTAINING SELF-DEVELOPING SUBSTRATE FOR USE IN ANALYSIS OF LIQUID

BACKGROUND OF THE INVENTION

1. Field of the Invention

The present invention relates to a dry analytical element containing self-developing substrate for use in analysis of liquid such as body fluid.

2. Description of Prior Art

Self-developing substrates capable of dissociating p-nitrophenol pigment have been widely utilized in recent years. Particularly, the amylase analysis method using glucosidase enzyme and G5PNP or G7PNP obtained by introducing p-nitrophenol pigment (herein referred to as PNP) into oligosaccharide (such as G5 or G7) is superior in assay and accuracy to the conventional pigment starch method (for instance, Methods of Enzymatic Analysis, page 894, by H. U. Bergmeyer) in which a pigment starch substrate obtained by dyeing starch with a reactive dye, such as blue starch or amylopectin azure is used and assay is carried out by forming a precipitate by utilizing a difference in molecular weight distribution. Further, the amylase analysis method has an advantage in that the continuous monitoring assay (rate assay in a narrow sense) can be conducted.

However, p-nitrophenol pigment is a pH indicator and hence, its absorbance is greatly affected by the pH in reaction systems. Accordingly, there is a disadvantage that dissociation state greatly varies depending on pH.

For instance, pK (logarithm of the reciprocal of dissociation constant) of p-nitrophenol is 7.2 and less than 50% of p-nitrophenol released from the substrate is dissociated at a pH of about 7.0 which is the optimum pH for amylase (see, Clinical Pathology, extra number of June, No. 55, page 205 by Shin Takaya, written in the Japanese language).

Accordingly, in the measurement of amylase activity by using G5PNP or G7PNP, there is widely adopted a method wherein the released p-nitrophenol pigment is perfectly dissociated by a two-step reaction comprising (a) an enzymatic reaction and (b) photometric measurement after the termination of the enzymatic reaction by the addition of a solution having a high pH and photometry is conducted (by increasing detection sensitivity) at the sacrifice of the original continuous monitoring assay function.

Even when the amylase analysis method using glucosidase enzyme and the modified oligosaccharide obtained by introducing p-nitropenol into oligosaccharide, is used in the dry analytical element, there are serious disadvantages that the dissociation of p-nitrophenol released by the amylase reaction and the glucosidase reaction is not satisfactory and sensitivity is low. Particularly, in integral multilayer analytical elements, layers are in fluid contact with each other and the pH of these layers are practically equal so that it has been difficult to meet the requirements for the optimum pH for amylase and glucosidase as well as the satisfactory dissociation of p-nitrophenol. Further, the method using the aforementioned two-step reaction severely damages the simplicity and speediness which are advantages claimed for the dry analytical method.

In the measurement of the activity of acid phosphatase by using p-nitrophenyl phosphate as a self-developing substrate, released p-nitrophenol is not dissociated at all and color formation does not occur, when the reagent layer of the integral multilayer analytical element buffers at a pH of 4 which is the optimum pH for enzyme. When the reagent layer is kept at a pH range within which p-nitrophenol is dissociated and develops a color, that is, the reagent layer is kept at a pH of 7.2 or above, the dissociation of p-nitrophenol from the substrate by enzyme does not proceed and p-nitrophenol does not develop a color in a short time.

SUMMARY OF THE INVENTION

It is an object of the present invention to provide a dry analytical element for use in the measurement of activity of enzyme which is active towards a self-developing substrate capable of dissociating p-nitrophenol, said substrate being incorporated in a water-retaining carrier, characterized in that the element is highly sensitive to an enzyme whose optimum pH lies in a pH range within which the dissociation of p-nitrophenol is insufficient for color formation.

There is provided by the present invention a dry analytical element for use in the measurement of activity of enzyme in aqueous liquids having one or more water-retaining layers which contains a self-developing (i.e., self-developable) substrate having a p-nitrophenol group attached to its molecular structure through an ether linkage or an ester linkage and a cationic polymer, said self-developing substrate and said cationic polymer being incorporated in the same water-retaining carrier (i.e., water-retainable carrier) or incorporated separately in different water-retaining carriers which are arranged to allow the layers to have liquid contact with each other.

DETAILED DESCRIPTION OF THE INVENTION

Typical examples of enzymes to be analyzed by the present invention are given in Table 1 wherein each self-developing substrate to be used in the analysis of each enzyme is exemplified. The enzyme to be analyzed may be alone or in a combination of two or more, for instance, a combination of amylase and glucosidase.

In addition to those given in Table 1, there can be used, as self-developing substrates for amylase, p-phenyl glucosides of oligosaccharides in where non-reducing end-groups are blocked. Examples of such substrates are disclosed in Japanese Patent Provisional Publication Nos. 59(1984)-31699 and 59(1984)-51800.

TABLE 1

| Enzyme | Self-developing substrate |
| --- | --- |
| N-acetyl-α-galactosaminidase | p-nitrophenyl-2-acetamido-2-deoxy-α-D-glucopyranoside |
| N-acetyl-β-glucosaminidase | p-nitrophenyl-2-acetamido-2-dioxy-β-D-glucopyranoside |
| β-galactosidase | o-nitrophenyl-β-D-galactopyranoside |
| β-glucuronidase | p-nitrophenyl-β-D-glucuronide |
| trypsin thrombin plasmin | p-nitrophenyl p'-guanidinobenzoate |
| amylase + α-glucosidase | p-nitrophenyl-α-D-maltheptaoside (PNP-G7) |
| | p-nitrophenyl-α-D-malthexaoside (PNP-G6) |
| | p-nitrophenyl-α-D-maltpentaoside (PNP-G5) |
| | p-nitrophenyl-α-D-maltoside (PNP-G2) |
| | p-nitrophenyl-α-D-malttetraoside (PNP-G4) |
| | p-nitrophenyl-α-D-maltrioside (PNP-G3) |

TABLE 1-continued

| Enzyme | Self-developing substrate |
| --- | --- |
| phosphatase (alkaline) | p-nitrophenyl phosphate disodium salt |
| phosphatase (acidic) | p-nitrophenyl phosphate (dicyclohexyl) ammonium salt p-nitrophenyl phosphate di-tris salt, etc. |
| phospholipase C | p-nitrophenyl phosphocholine |
| phosphodiesterase | p-nitrophenylthymidine-5′ phosphate |

The cationic polymers which can be used in the present invention are polymers containing secondary and tertiary amino groups, polymers having nitrogen-containing heterocyclic moiety, and quaternary cationic group-containing polymers with molecular weights in the range of 5,000 to 200,00, particularly 10,000 to 50,000.

Examples of such polymers include vinylpyridine polymers and cationic vinylpyridinium polymers disclosed in U.S. Pat. Nos. 2,548,564, 2,484,430, 3,148,061 and 3,756,814 and Japanese Patent Provisional Publication No. 52(1977)-136626; gelatin-crosslinkable polymers disclosed in U.S. Pat. Nos. 3,625,694, 3,859,096 and 4,128,538 and U.K. Patent No. 1,277,453; aqueous sol type cationic polymers disclosed in U.S. Pat. Nos. 3,958,995, 2,721,852 and 2,798,063 and Japanese Patent Provisional Publication Nos. 54(1979)-115228, 54(1979)-145529 and 54(1979)-126027; water-insoluble cationic polymers disclosed in U.S. Pat. No. 3,898,088 and Japanese Patent Provisional Publication No. 55(1980)-33172; reactive mordants capable of forming cavalent bond with dyes disclosed in U.S. Pat. No. 4,168,976 (Japanese Patent Provisional Publication No. 54(1979)-137333); cationic polymers disclosed in U.S. Pat. Nos. 3,709,690, 3,788,855, 3,642,482, 3,488,706, 3,557,066, 3,271,147 and 3,271,148 and Japanese Patent Provisional Publication Nos. 50(1975)-71332, 53(1978)-30328, 52(1977)-15528, 53(1978)-125 and 53(1978)-1024; and cationic polymers disclosed in U.S. Pat. Nos. 2,675,316 and 2,882,156.

Among them, those preferred exhibit minimal those which hardly migration from the hydrophilic colloid layers to other layer. For instance, preferred are polymers capable of crosslinking with hydrophilic colloids of gelatin, water-insoluble cationic polymers and aqueous sols (or latex dispersions).

The following cationic polymers are particularly preferred.

(1) Polymers having quaternary ammonium group and a group capable of forming covalent bonds with gelatin (e.g., aldehyde, chloroalkanoyl, chloroalkyl, vinylsulfonyl, pyridiniumpropionyl, vinylcarbonyl and alkylsulfonoxy groups), such as the compound having the following formula:

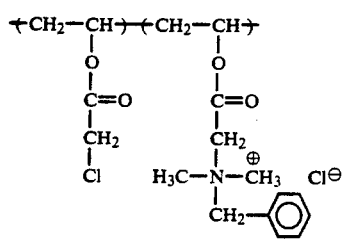

(2) Reaction products of a crosslinking agent (e.g., bisalkanesulfonate or bisallenesulfonate) with a copolymer composed of a monomer repeating unit having the formula (VII) and another ethylenically unsaturated monomer repeating unit:

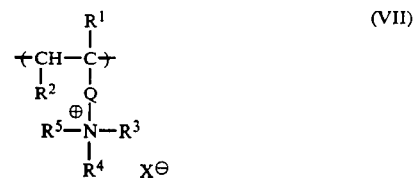

wherein $R^1$ is hydrogen or an alkyl group; $R^2$ is hydrogen, alkyl or aryl group; Q is a divalent group; $R^3$, $R^4$ and $R^5$ are alkyl or aryl groups or at least two of $R^3$, $R^4$ and $R^5$ may be combined together to form a heterocyclic ring; and X is an anion (the above alkyl and aryl groups may be unsubstituted or substituted):

(3) Polymers having the formula (VIII):

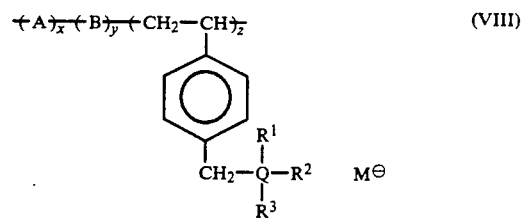

wherein x is about 0.25 to about 5 mole %; y is about 0 to about 90 mole %; z is about 10 to about 99 mole %; A is a monomer containing at least two ethylenically unsaturated bonds; B is a copolymerizable ethylenically unsaturated monomer; Q is nitrogen or phosphorus; $R^1$, $R^2$ and $R^3$ are alkyl or cyclic hydrocarbon groups or at least two or $R^1$, $R^2$ and $R^3$ may be combined together to form a ring (these groups and the ring may be unsubstituted or substituted).

(4) Copolymers composed of component (a) having the formula (IX), component (b) and component (c):

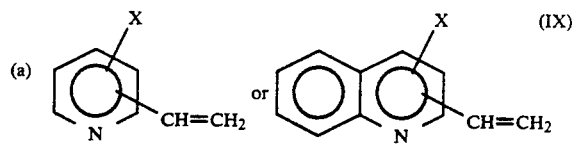

wherein X is hydrogen, an unsubstituted or substituted alkyl group or halogen;

(b) an acrylate ester;

(c) acrylonitrile:

(5) Water-insoluble polymers containing a repeating unit having the formula (X) in a ratio of at least ⅓ of the whole:

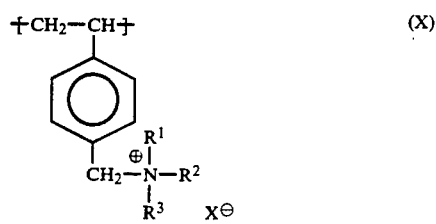

wherein $R^1$, $R^2$ and $R^3$ are each an unsubstituted or substituted alkyl with the proviso that the sum of carbon atoms of $R^1$, $R^2$ and $R^3$ is 12 or more.

The present invention can be applied to known various dry analytical elements. Particularly, the present invention is suitable for use in elements containing a solid support which allows any of the self-developing substrate, the cationic polymer and liquids to be analyzed to permeate therethrough. The element may be composed of a single layer or a multilayer comprising reagent layer, reflecting layer, porous spreading layer, light-blocking layer, filtering layer, registration layer, water absorbing layer, support, undercoating layer and other known layers. Such analytical elements are disclosed in U.S. Pat. Nos. 3,992,158 and 4,042,335.

The following structures are practically preferred, when a support is used:

(1) an element comprising a liquid spreading layer which also functions as a reagent layer on a support;

(2) an element having such a structure that a water absorbing layer is provided on a support and a liquid spreading layer also functioning as a reagent layer is provided thereon;

(3) an element comprising a reagent layer and a liquid spreading layer on a support:

(4) an element comprising a water absorbing layer, a reagent layer and a liquid spreading layer in this order on a support;

(5) an element comprising a reagent layer, a reflecting or filtering layer and a liquid spreading layer in this order on a support; and (6) an element comprising a water-absorbing layer, a reagent layer, a filtering layer and a liquid spreading layer in this order on a support.

In one preferred embodiment of the analytical element of the invention, the analytical element is in the form of a multilayer analytical element comprising a water-impermeable support and a porous liquid-spreading layer having a liquid metering effect in which the porous liquid-spreading layer containing the self-developing substrate and the cationic polymer.

In another preferred embodiment of the analytical element of the invention, the analytical element is in the form of a multilayer analytical element comprising a water-impermeable support, a water-retaining layer and a porous liquid-spreading layer having a liquid metering effect, said water-retaining layer being arranged to show the relationship of liquid contact with the spreading layer, and said porous liquid-spreading layer containing the self-developing substrate and the water-retaining layer containing the cationic polymer.

Detecting reagents which are used in the dry analytical element of the present invention can be used for the measurement of the activity of various enzymes in liquid samples. The dry analytical element of the present invention can be used for the measurement of the activity of any enzyme which cause the self-developing substrate to release p-nitrophenol.

Further, the dry analytical element can be used for the measurement of the concentrations of substances or the activity of enzymes other than those described above, when the above detecting reaction is coupled with other chemical reaction. In this case, reagents required for the chemical reaction to be coupled are incorporated in the detecting reagent.

For instance, coupled reaction reagents may be incorporated in the spreading layer or an auxiliary spreading layer provided on said spreading layer according to the reaction type, such as, enzyme tagged antigen, enzyme tagged antibody, antigen, antibody, etc. in enzyme tagged immunity analysis. Preferred enzyme are alkaline phosphatase and galactosidase.

If desired, a hydrophilic polymer, a buffering agent or fine light-blocking particles may be incorporated in the layer containing the self-developing substrate of the dry analytical element of the present invention.

Examples of the hydrophilic polymers include starch, cellulose, agarose, gelatin and derivatives thereof (e.g., hydroxymethylated derivatives, hydroxypropylated derivatives), acrylamide polymers, copolymers of acrylamide with various vinyl monomers, vinylpytrrolidone polymers, copolymers of vinylpyrrolidone with various vinyl monomers, acrylate polymers and copolymers of an acrylate with various vinyl monomers. Among them, vinylpyrrolidone polymers, acrylamide polymers and cellulose derivatives are preferred.

When said hydrophilic polymer is incorporated in the spreading layer containing self-developing substrate, the polymer is used in an amount of about 2 to about 15 $g/m^2$, preferably about 2 to 10 $g/m^2$.

Examples of the buffering agent which can be incorporated in the layer containing the self-developing substrate of the dry analytical element of the invention include known buffering agents such as carbonates, borates, phosphates and Good's buffering agent. These buffering agents can be chosen by referring to the literature "Experimental Method for Protein and Enzyme" written in Japanese by T. Horio et al. (Nankodo, 1981).

The layer containing the self-developing substrate may contain fine light-blocking particles which can also be used in a light-blocking layer described hereinafter.

The self-developing substrate and optionally, the hydrophilic polymer, the buffering agent or the light-blocking particles can be incorporated in the layer, in which said substrate is to be contained, by coating or spraying a coating solution containing said reagent, etc. on the spreading layer and drying it.

When the layer containing the self-developing substrate is the spreading layer composed of woven fabric, knitted fabric, nonwoven fabric or glass fiber filter paper, the spreading layer may be immersed in a solution containing the reagents, etc. and dried. When the spreading layer is to be laminated to form an integral multilayer analytical element, the immersed spreading layer in a dry state or in a semidry state may be laminated onto other layer.

When a layer to be formed by coating is one composed of brushed polymer layer or three-dimensional lattice structure of microbeads, a mixture of a coating solution for this layer and the above coating solution containing said reagents, etc. may be applied.

Layers containing the detecting reagent may be composed of two or more layers in the present invention. The self-developing substrate and the cationic polymer may be uniformly incorporated in all layers. However, it is preferred that more self-developing substrate is distributed in a layer far away from the support and more cationic polymer is distributed in a layer near the support.

Examples of the water-impermeable light-transmissive supports used in the dry analytical element of the present invention include a transparent film or sheet of about 50 $\mu m$ to about 1 mm, preferably about 80 to about 300 $\mu m$ in thickness, made of a polymer such as polyethylene terephthalate, polycarbonate of bisphenol A, polystyrene and cellulose esters (e.g. cellulose diacetate, cellulose triacetate, celulose acetate propionate, etc.).

A light-reflecting support which can be used in the element of the present invention can be easily prepared by incorporating a light-reflecting coloring material in said polymer. Alternatively, the support may be prepared by applying the light-reflecting coloring material to the surface of the transparent support made of said polymer, or by sticking a pressure-sensitive adhesive tape containing said coloring material on the surface of the support.

There may be provided an undercoating layer on the support to enhance the adhesion between the support and a water absorbing layer or a layer containing a detecting reagent and a carboxylic acid coenzyme stabilizer provided on the support. Instead of providing the undercoating layer, the surface of the support may be activated by physical or chemical treatment to enhance the adhesion.

When the dry analytical element of the invention is an intergral multilayer analytical element, a water absorbing layer is provided on the water-impermeable, light-transmissive support (optionally, intervened by other layer such as undercoating layer). Preferably, the water-absorbing layer of the dry analytical element in the present invention should be a layer comprising a hydrophilic binder, that is, a layer containing, as a layer-forming component, a hydrophilic polymer which absorbs water to swell.

The hydrophilic polymer used in the water-absorbing layer is a natural or synthetic hydrophilic polymer showing a swelling ratio of about 1.5 to about 20, preferably about 2.5 to 15 at 30° C. when the polymer absorbs water. Examples of the hydrophilic polymers include gelatin (e.g. acid-processed gelatin, deionized gelatin, etc.), gelatin derivatives (e.g. phthalated gelatin, hydroxyacrylate-grafted gelatin, etc.), agarose, pullulan, pullulan derivatives, polyacrylamide, plyvinyl alcohol and polyvinyl pyrrolidon. Anionic polymers such as polyacrylic acid and polystyrenesulfonic acid are not preferred.

The dry thickness of the water-absorbing layer ranges preferably from approx. 1 μm to approx. 100 μm, more preferably from approx. 3 μm to approx. 30 μm. It is preferred that the water-absorbing layer is substantially transparent. If desired, the water-absorbing layer may contain a surfactant (nonionic and ampholytic surfactants being preferred) and a buffering agent.

Preferably, the cationic polymer which is an essential ingredient of the present invention is incorporated in the water absorbing layer. The cationic polymer is used in an amount of about 5 to about 70% by weight based on the entire amount of the hydrophilic polymer, but the amount varies depending on the type of the polymer.

If desired, there may be provided a light-blocking layer on the water-absorbing layer. The light-blocking layer is a water-permeable layer in which fine particles or fine powder having light-blocking properties or light-blocking and light-reflecting properties (hereinafter referred to simply as fine light-blocking particle) are dispersed in a small amount of a film-forming hydrophilic polymer binder. The light-blocking layer functions as a light-reflecting layer or a background layer as well as blocker to the color of an aqueous liquid spotted on the spreading layer containing the detecting reagent and a carboxylic acid, such as the red of hemoglobin in a whole blood sample, when a detectable change (a color change, a color formation, etc.) in the water-absorbing layer is measured from the side of the light-transmissive support by reflection photometry.

Examples of the light-blocking and light-reflecting particles include fine titanium dioxide particles (rutile type, anatase type and brookite type microcrystalline particles having a particle size of about 0.1 to about 1.2 μm), fine barium sulfate particles and fine aluminum particles or flakes. Examples of the fine light-blocking particles include carbon black, gas black and carbon microbeads. Among them, fine titanium dioxide particles and fine barium sulfate particles are preferred. Most preferred are anatase type fine titanium dioxide particles.

Examples of the hydrophilic polymer binders used in the light-blocking layer include weakly hydrophilic polymers such as regenerated cellulose and cellulose acetate as well as the hydrophilic polymers employable in the water-absorbing layer. Among them, gelatin, gelatin derivatives and polyacrylamide are preferred. Gelatin and gelatin derivatives may be used together with known curing agents (crosslinking agents).

The light-blocking layer can be provided in such a manner that an aqueous dispersion containing the fine light-blocking particles and the hydrophilic polymer is coated on the water-absorbing layer and then dried by any of conventional methods. Instead of providing the light-blocking layer, the fine light-blocking particles may be incorporated in the spreading layer.

There may be provided an adhesive layer on the water-absorbing layer, optionally intervened by other layer such as the light-blocking layer to bond the spreading layer. The adhesive layer is preferably formed from a hydrophilic polymer which can bond the spreading layer to other layer while the polymer is wetted or swelled with water. Examples of the hydrophilic polymers include those employable in the water absorbing layer. Among them, gelatin, gelatin derivatives and polyacrylamide are preferred. The dry thickness of the adhesive layer generally ranges from approx. 0.5 μm to approx. 20 μm, preferably from approx. 1 μm to approx. 10 μm. If desired, the adhesive layer may be provided on other layers as well as on the water-absorbing layer to enhance the adhesion between layers. The adhesive layer can be prepared in such a manner that an aqueous solution containing the hydrophilic polymer and optionally other agents such as surfactant is coated on the support, the water-absorbing layer or other layer.

The spreading layer preferably has a liquid metering effect. The term "liquid metering effect" used herein refers to a function capable of spreading a liquid sample spotted on the spreading layer in such a manner that the spread area of the liquid is approximately in proportion to the amount of the liquid when the liquid is applied thereon.

Examples of materials for the matrix of the spreading layer include filter paper, nonwoven fabric, woven fabric (e.g. plain weave fabrics such as broadcloth and poplin), knitted fabric (e.g. tricot knitted cloth, double tricot knitted cloth and milanese knitted cloth), glass fiber filter paper, membrane filter made of brush polymer and three-dimensional lattice structure made of polymer microbeads. Among them, woven fabric and knitted fabric are preferred, because a fibrous layer composed of woven or knitted fabric can well retain the reagents, etc. Such preferred layers are described in more detail in Japanese Patent Provisional Publication Nos. 55(1980)-164356, 57(1982)-66359 and 60(1985)-222769.

As the woven fabric and the knitted fabric used for the dry analytical element of the invention, there are preferred the fabrics from which deposited oils and fats are substantially removed by a degreasing treatment when yarn or fabric is prepared or knitting is conducted.

When the woven fabric or the knitted fabric is used in the spreading layer of the integral multilayer analytical element, the fabrics may be processed to make them hydrophilic to enhance the adhesion to an underlying layer (near to the support). Examples of such processes for making the fabrics hydrophilic include physical activating process (preferably glow discharge process or corona discharge process) disclosed in Japanese Patent Provisional Publication No. 57(1982)-66359 wherein at least one side of the cloth is processed, hydrophilic polymer impregnating process disclosed in Japanese Patent Provisional Publication Nos. 55(1980)-164356 and 57(1982)-66359 and a process disclosed in Japanese Patent Provisional Publication No. 60(1985)-222770. These process may be carried out either alone or in combination.

In preparing the integral multilayer analytical element, the spreading layer constituted of woven fabric or knitted fabric can be laminated onto the water absorbing layer or the adhesive layer according to the processed disclosed in Japanese Patent Provisional Publication Nos. 55(1980)-164356 and 57(1982)-66359. For instance, the woven or knitted fabric is laminated onto the water-absorbing layer or the adhesive layer while applying uniformly, slightly pressure thereto, said layer being still wet after coating or being wetted or swelled with water (or water containing a small amount of a surfactant) after drying.

The spreading layer composed of brushed polymer or membrane filter can be provided according to the method described in Japanese Patent Publication No. 53(1978)-21677, that composed of three-dimensional lattice structure made of polymer microbeads can be provided according to the method described in Japanese Patent Provisional Publication No. 55(1980)-90859, and that composed of filter paper or nonwoven fabric can be provided according to the method described in Japanese Patent Provisional Publication No. 57(1982)-148250.

When the hydrophilic polymer binder for the water-absorbing layer or the adhesive layer is gelatin or a derivative thereof, a material (woven fabric or knitted fabric) for the spreading layer may be laminated onto said layer while gelatin (or derivative) is still in the form of undried gel after coating.

It is possible that the dry analytical element of the present invention is composed of a single sheet consisting of a layer containing the self-developing substrate and the cationic polymer.

When the dry analytical element of the invention is in the form of an integral multilayer analytical element, it is preferred from the viewpoints of production, packaging, transportation, storage and measuring operation that the element is cut into pieces 15 to 30 mm square or circles having a diameter of 15 to 30 mm and put into a slide frame to form an analytical slide as described in Japanese Patent Provisional Publication Nos. 57(1982)-63452 and 54(1979)-156079, Japanese Utility Model Provisional Publication Nos. 56(1981)-142454 and 58(1983)-32350 and Japanese Patent Provisional Publication No. 58(1983)-501144.

About 5 to about 30 $\mu l$, preferably about 8 to about 15 $\mu l$ of an aqueous liquid sample is spotted (deposited) on the spreading layer of the dry analytical element of the present invention. Optionally, the analytical element is then incubated at a substantially constant temperature ranging from about 20° to about 45° C. A detectable change such as change in color or color formation within the element is measured from one side of the element (from the side of the light-transmissive support when the integral multilayer analytical element is used) by reflection photometry, and a substance to be analyzed (analyte in the liquid sample) is analyzed by the principle of colorimetry.

Enzyme having the optimum pH in a pH range within which p-nitrophenol is insufficiently dissociated or substantially not dissociated, can be analyzed with sufficiently high sensitivity by using the dry analytical element of the present invention for use in the analysis of aqueous liquids, said element having a water-retaining carrier containing a self-developing substrate capable of dissociating p-nitrophenol. The analysis of amylase by using G5-PNP or G7-PNP, or the analysis of acid phosphatase by using p-nitrophenol phosphate can be made with high sensitivity.

The following examples are provided to illustrate the present invention without limiting it thereto.

EXAMPLE 1

Membrane filter FM 300 (manufactured by Fuji Photo Film Co., Ltd.) composed of cellulose acetate was impregnated with an aqueous solution containing the following ingredients, and dried.

| | |
|---|---|
| p-Nitrophenyl-α-D-maltheptaoside | 100 mg |
| α-Glucosidase | 150 U |
| 0.5 M Phosphate buffering agent (pH 7.0) | 10 ml |
| Poly-co-(styrene-N-methylmorpholinium methylstyrene-divinylbenzene) 55:43:2 (50% latex solution) | 2 ml |

The resulting impregnated filter was cut into pieces 10 mm square and each piece was fixed to a plastic piece by means of a double-coated adhesive tape to prepare a dry analytical element for use in the detection of amylase.

10 $\mu l$ of each of serums or diluted saliva solutions containing enzyme at different concentrations was deposited on the element which was then colored yellow. Amylase activity could be visually determined by the comparison with standard color, or the activity could be determined by a calibration curve with a reflection densitometer at a measuring wavelength of 400 nm.

The calibration curve was prepared in the following manner.

10 $\mu l$ of each of ten kinds of serums containing enzyme at known concentrations was deposited on the element and reacted at 37° C. for about 5 minutes. The reflection density of each serum was measured after completion of the incubation for two minutes and five minutes. The amount ($\Delta OD$) of color formation for three minutes was determined as a difference between OD values for three minutes and for five minutes. Each of $\Delta OD$ values was correlated with each of enzyme activity values to prepare the calibration curve.

EXAMPLE 2

The surface of a colorless transparent smooth polyethylene terephthalate film having a gelatin undercoating layer and a thickness of 180 μm, was coated with an aqueous solution having the following composition in such an amount as to give a dry film thickness of 10 μm (in a coating amount of 100 g/m²), and the coated film was dried.

| | |
|---|---|
| Gelatin | 300 g |
| Surfactant 10 G (Olin Corp.) | 5 g |
| Poly-co-(styrene-N-methylmorpholinium methylstyrene-divinylbenzene) polymerization ratio 55:43:2 (15% latex solution) | 280 g |
| Water | 2,150 g |

(The pH of the aqueous solution was adjusted to 7.0 with a dilute NaOH solution)

The above gelatin layer was wetted by uniformly supplying water in a rate of about 30 g/m² to the whole surface thereof. A tricot knitted fabric (made of polyester, 40 gauges) was laminated thereon under slight pressure, and the resulting laminate was dried.

The surface of the fabric was uniformly coated with an aqueous solution having the following composition in a coating amount of 200 cc/m² and dried to prepare an integral multilayer analytical element for the measurement of amylase.

| | |
|---|---|
| p-Nitrophenyl-α-D-maltheptaoside | 0.6 g |
| α-Glcosidase | 160 mg |
| NaCl | 90 mg |
| Water | 17 g |
| Potassium phosphate (pH 7.0) | 0.6 g |

For the purpose of comparison, an integral multilayer analytical element for the measurement of α-amylase was prepared in the same manner as that described in Example 1 except that the poly-co-(styrene-N-methylmorpholinium methylstyrene-divinylbenzene) 55:43:2 in the gelatin layer was omitted.

10 μl of each of control serums (commercially available control serum or those containing optionally human saliva amylase added thereto) having amylase activity of 0, 72, 308, 882 and 1200 IU/L was deposited on each of the analytical elements of Example 2 according to the present invention and Comparison Example. The elements were incubated at 37° C. Change in reflection density per minute during the passage of time from three minutes to six minutes was measured with a light of 400 nm.

The results are shown in Table 2.

TABLE 2

| | Present invention | Comparison |
|---|---|---|
| 0 IU/L | 0.000 | 0.000 |
| 72 IU/L | 0.012 | 0.008 |
| 388 IU/L | 0.037 | 0.027 |
| 1200 IU/L | 0.071 | 0.053 |

It is apparent from Table 2 that the analytical element for the measurement of amylase obtained by adding poly-co-(styrene-N-methylmorpholiniummethylstyrene-divinylbenzene) 55:43:2 to the color forming layer according to the present invention has higher sensitivity than that of the analytical element for comparison.

REFERENCE EXAMPLE

10 μl of each of aqueous solutions containing p-nitrophenol (PNP) at various concentrations was deposited on each of the multilayer analytical element of Example 2 of the present invention and Comparison Example. After 10 minutes, reflection density was measured with a light of 400 nm. The results are shown in Table 3.

TABLE 3

| | Multilayer analytical element | |
|---|---|---|
| Concn. of PNP | Present invention | Comparison Example |
| 1 μm | 0.755 | 0.569 |
| 2 μm | 0.953 | 0.697 |
| 3 μm | 1.177 | 0.795 |
| 4 μm | 1.240 | 0.907 |

It is apparent from Table 3 that the integral multilayer analytical element (Example 2) for the measurement of amylase obtained by adding poly-co-(styrene-N-methylmorpholiniummethylstyrene-divinylbenzene) to the gelatin layer has high detection sensitivity as compared with that of the element for comparison.

EXAMPLE 3

A multilayer analytical element for the measurement of acid phosphatase activity was prepared in the following manner.

(1) Support

An undercoated polyethylene terephthalate film of 150 μm in thickness.

(2) Color forming layer

The surface of the support was coated with a coating solution having the following composition in such an amount as to give a dry film of 10 μm in thickness, and dried.

| | |
|---|---|
| Alkali-treated deionized gelatin | 40 g |
| Water | 642.5 g |
| Nonylphenoxy polyglycidol | 4.5 g |
| Poly-co-(styrene-N-methylpiperidinium methylstyrene) polymer 55:45 | 250 g |

(3) Buffering layer

The surface of the color forming layer was coated with a coating solution having the following composition in such an amount as to give a dry film of 10 μm in thickness, and dried.

| | |
|---|---|
| Deionized gelatin | 96 g |
| Nonylphenoxy polyglycidol | 5.5 g |
| Citrate buffering solution (pH 5.0) (0.1 mole/l) | 800 g |
| 1,2-Bis(vinylsulfonylacetamide)ethane | 2 g |

(4) Adhesive layer

The surface of the buffering layer was coated with a coating solution having the following composition in such an amount as to give a dry film of 5 μm in thickness, and dried.

| | |
|---|---|
| Gelatin | 40 g |
| Water | 934.6 g |
| Nonylphenoxy polyglycidol | 4.3 g |

(5) Liquid spreading layer

The surface of the adhesive layer was coated with an aqueous solution of 0.4% nonylphenoxy polyglycidol. A composed of polyethylene terephthalate spun yarn (50 D, 36 gauges) was laminated thereon under pressure to form a liquid spreading layer.

(6) Impregnation of self-developing substrate

A solution having the following composition was coated on the liquid spreading layer.

| | |
|---|---|
| p-Nitrophenyl phosphate dicyclohexylamine salt | 30 mmole |
| Polyvinyl pyrrolidone having an average molecular weight of 100,000 | 5 g |
| Ethanol | 20 g |
| Acetone | 25 g |

An integral multilayer analytical element for the measurement of acid phosphatase activity according to the present invention was prepared by the above-described manner.

For the purpose of comparison, an analytical element for the measurement of acid phosphatase activity was prepared in the same manner as that described in Example 3 except that poly-co-(styrene-N-methyl-piperidinium methylstyrene) 55:45 was omitted.

Each slide was put into a plastic mount described in Japanese Patent Provisional Publication No. 57(1982)-63452. 10 μl of each of standard solutions having activity value of 300, 600 and 1200 U/L prepared from control serum and resistant phosphatase originated from human serum, was spotted on each mount, and the element was incubated at 37° C. for 10 minutes, while preventing water from evaporating by sealing the mount with a polyester tape. During the incubation, reflection density was measured with a light having a wavelength of 400 nm.

The results are shown in Table 4 wherein ΔOD represents a difference in reflection density between 5 minutes incubation and 2 minute incubation after spotting.

TABLE 4

| Content of acid phosphatase | ΔOD (5 min.–2 min.) | |
|---|---|---|
| | Present invention | Comparison Example |
| 300 U/L | 0.05 | 0.0002 |
| 605 | 0.98 | 0.0004 |
| 1200 | 0.152 | 0.0008 |

Little change in absorbance was caused in Comparative Example, though enzyme existed.

We claim:

1. A dry analytical element for measurement of activity in an aqueous liquid of an enzyme, having one or more water-retaining layers and said enzyme having an optimum pH in a pH range with which the dissociation of p-nitrophenol is insufficient for color formation, said layers comprising a self-developing substrate having a p-nitrophenol group attached to its molecular structure through an ether linkage or an ester linkage, and a cationic polymer, said self-developing substrate and said cationic polymer being incorporated in the same water-retaining layer or incorporated separately in different water-retaining layers which are arranged to allow the layers to have liquid contact with each other, whereby the cationic polymer allows the p-nitrophenol to be released.

2. The analytical element as claimed in claim 1, wherein said element comprises a water-impermeable support and a porous liquid-spreading layer having a liquid metering effect, said porous liquid-spreading layer containing the self-developing substrate and the cationic polymer.

3. The analytical element as claimed in claim 1, wherein said element comprises a water-impermeable support, a water-retaining layer and a porous liquid-spreading layer having a liquid metering effect, said water-retaining layer being arranged to allow the layers to have liquid contact with the spreading layer, and said porous liquid-spreading layer containing the self-developing substrate and the water-retaining layer containing the cationic polymer.

4. The analytical element as claimed in claim 1, wherein the cationic polymer is a polymer having a quaternary ammonium group and a group capable of forming a covalent bond with gelatin.

5. The analytical element as claimed in claim 1, wherein the cationic polymer is a reaction product of a crosslinking agent and a copolymer composed of a repeating unit of the formula:

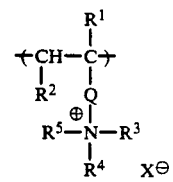

wherein $R^1$ is hydrogen or an alkyl group; $R^2$ is hydrogen, alkyl or aryl group; Q is a divalent group; $R^3$, $R^4$ and $R^5$ are alkyl or aryl groups or at least two of $R^3$, $R^4$ and $R^5$ may be combined together to form a heterocyclic ring; and X is an anion, in which the above alkyl and aryl groups may be unsubstituted or substituted, and a repeating unit derived from another ethylenically unsaturated monomer.

6. The analytical element as claimed in claim 1, wherein the cationic polymer is a polymer having the formula:

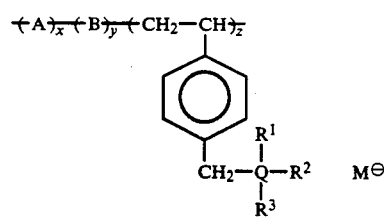

wherein x is about 0.25 to about 5 mole %; y is about 0 to about 90 mole %; z is about 10 to about 99 mole %; A is a repeating unit derived from a monomer containing at least two ethylenically unsaturated bonds; B is a repeating unit derived from a copolymerizable ethylenically unsaturated monomer; Q is nitrogen or phosphorus; $R^1$, $R^2$ and $R^3$ are alkyl or cyclic hydrocarbon groups or at least two of $R^1$, $R^2$ and $R^3$ may be combined together to form a ring, in which $R^1$, $R^2$ and $R^3$ and the ring may be unsubstituted or substituted.

7. The analytical element as claimed in claim 1, wherein the cationic polymer is a copolymer composed of (a) a component having the formula:

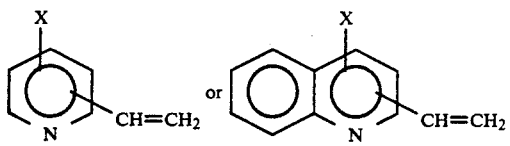

wherein X is hydrogen, an unsubstituted or substituted alkyl group or halogen;

(b) an acrylate ester; and (c) acrylonitrile.

8. The analytical element as claimed in claim 1, wherein the cationic polymer is a water-insoluble polymer containing a repeating unit having the formula:

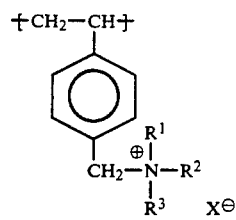

wherein each of $R^1$, $R^2$ and $R^3$ is an unsubstituted or substituted alkyl with the proviso that the sum of carbon atoms of $R^1$, $R^2$ and $R^3$ is 12 or more, in an amount of at least one third of the total repeating of the polymer.

9. The analytical element as claimed in claim 1 wherein said enzyme is selected from the group consisting of N-acetyl-α-galactosaminidase, N-acetyl-β-glucosaminidase, β-galactosidase, β-glucuronidase, trypsin, thrombin, plasmin, amylase, α-glucosidase, alkaline phosphatase, acidic phosphatase, phospholipase C, and phosphodiesterase.

10. The analytical element as claimed in claim 1 wherein said enzyme is amylase.

11. The analytical element as claimed in claim 1 wherein said enzyme is acidic phosphatase.

* * * * *

UNITED STATES PATENT AND TRADEMARK OFFICE
CERTIFICATE OF CORRECTION

PATENT NO. : 5,077,011
DATED : December 31, 1991
INVENTOR(S) : Yoshikazu Amano; Kaoru Terashima; Harumi Katsuyama It is certified that error appears in the above-identified patent and that said Letters Patent is hereby corrected as shown below:

Title page, item

[75] Inventors: Yoshikazu Amano; Kaoru Terashima; Harumi Katsuyama, all of Asaka, Japan Signed and Sealed this Twenty-second Day of June, 1993

Attest:

MICHAEL K. KIRK

*Attesting Officer*     Acting Commissioner of Patents and Trademarks